(12) United States Patent
Minning et al.

(10) Patent No.: US 7,172,997 B2
(45) Date of Patent: Feb. 6, 2007

(54) LIPOLYTIC ENZYME VARIANT

(75) Inventors: Stefan Minning, Frederiksberg C (DK); Jesper Vind, Vaerlose (DK); Sanne O. Schroder Glad, Ballerup (DK); Steffen Danielsen, Kobenhavn O (DK); Kim Borch, Birkerod (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 11/453,670

(22) Filed: Jun. 15, 2006

(65) Prior Publication Data

US 2006/0229223 A1    Oct. 12, 2006

Related U.S. Application Data

(63) Continuation of application No. 10/250,522, filed as application No. PCT/DK02/00016 on Jan. 10, 2002, now abandoned.

(60) Provisional application No. 60/262,579, filed on Jan. 18, 2001.

(30) Foreign Application Priority Data

Jan. 10, 2001   (DK) ............................... 2001 00032

(51) Int. Cl.
*C12N 9/16*   (2006.01)
*C12N 9/20*   (2006.01)
*C12N 1/20*   (2006.01)
*C07H 21/04*  (2006.01)

(52) U.S. Cl. .................. 510/226; 435/196; 435/198; 435/252.3; 435/320.1; 536/23.2; 536/23.7

(58) Field of Classification Search ................ 510/226; 435/196, 198, 252.3, 320.1; 536/23.2, 23.7
See application file for complete search history.

(56) References Cited

U.S. PATENT DOCUMENTS 5,869,438 A    2/1999    Svendsen et al.

FOREIGN PATENT DOCUMENTS

| | | |
|---|---|---|
| EP | 0 374 700 | 6/1990 |
| WO | WO 88/02775 | 4/1988 |
| WO | WO 92/05249 | 4/1992 |
| WO | WO 92/13130 | 8/1992 |
| WO | WO 92/19726 | 11/1992 |
| WO | WO 94/01541 | 1/1994 |
| WO | WO 97/07202 | 2/1997 |
| WO | WO 00/32758 | 6/2000 |
| WO | WO 01/83770 | 11/2001 |

OTHER PUBLICATIONS

Abstract of Japanese Patent No. JP 1994-230046, Accession No. 1996:328593 Caplus.

*Primary Examiner*—Tekchand Saidha
(74) *Attorney, Agent, or Firm*—Elias J. Lambiris

(57) ABSTRACT

The present invention relates to lipolytic enzyme variants with improved thermostability are obtained by substituting certain specified amino acid residues in a fungal lipolytic enzyme. The thermostable lipolytic enzyme variants are useful, e.g., for controlling pitch troubles in a process for the production of mechanical pulp or a paper-making process using mechanical pulp.

19 Claims, No Drawings

SEQUENCE LISTING

<160> NUMBER OF SEQ ID NOS: 22

<210> SEQ ID NO 1
<211> LENGTH: 269
<212> TYPE: PRT
<213> ORGANISM: Thermomyces lanuginosus

```
<400> SEQUENCE: 1

Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
                20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
                100                 105                 110

Phe Thr Ser Ser Trp Arg Ser Val Ala Asp Thr Leu Arg Gln Lys Val
                115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
                180                 185                 190

Leu Tyr Arg Ile Thr His Thr Asn Asp Ile Val Pro Arg Leu Pro Pro
                195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260                 265

<210> SEQ ID NO 2
<211> LENGTH: 269
<212> TYPE: PRT
<213> ORGANISM: Rhizomucor miehei

<400> SEQUENCE: 2

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
                20                  25                  30

Ile Pro Gly Ala Thr Trp Asp Cys Ile His Cys Asp Ala Thr Glu Asp
            35                  40                  45

Leu Lys Ile Ile Lys Thr Trp Ser Thr Leu Ile Tyr Asp Thr Asn Ala
    50                  55                  60

Met Val Ala Arg Gly Asp Ser Glu Lys Thr Ile Tyr Ile Val Phe Arg
65                  70                  75                  80

Gly Ser Ser Ser Ile Arg Asn Ala Ile Ala Asp Leu Thr Phe Val Pro
                85                  90                  95
```

|  |  |  |  |  |  |  |  |  |  |  |  |
|---|---|---|---|---|---|---|---|---|---|---|---|
| Val | Ser | Tyr | Pro | Pro | Val | Ser | Gly | Thr | Lys | Val | His | Lys | Gly | Phe | Leu |
|  |  |  | 100 |  |  |  |  | 105 |  |  |  | 110 |  |  |  |

```
             Val Ser Tyr Pro Pro Val Ser Gly Thr Lys Val His Lys Gly Phe Leu
                         100                 105                 110

Asp Ser Tyr Gly Glu Val Gln Asn Glu Leu Val Ala Thr Val Leu Asp
                         115                 120                 125

Gln Phe Lys Gln Tyr Pro Ser Tyr Lys Val Ala Val Thr Gly His Ser
                         130                 135                 140

Leu Gly Gly Ala Thr Ala Leu Leu Cys Ala Leu Gly Leu Tyr Gln Arg
             145                 150                 155                 160

Glu Glu Gly Leu Ser Ser Ser Asn Leu Phe Leu Tyr Thr Gln Gly Gln
                             165                 170                 175

Pro Arg Val Gly Asp Pro Ala Phe Ala Asn Tyr Val Val Ser Thr Gly
                         180                 185                 190

Ile Pro Tyr Arg Arg Thr Val Asn Glu Arg Asp Ile Val Pro His Leu
                         195                 200                 205

Pro Pro Ala Ala Phe Gly Phe Leu His Ala Gly Glu Glu Tyr Trp Ile
                         210                 215                 220

Thr Asp Asn Ser Pro Glu Thr Val Gln Val Cys Thr Ser Asp Leu Glu
             225                 230                 235                 240

Thr Ser Asp Cys Ser Asn Ser Ile Val Pro Phe Thr Ser Val Leu Asp
                             245                 250                 255

His Leu Ser Tyr Phe Gly Ile Asn Thr Gly Leu Cys Ser
                             260                 265

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
ttgaattgaa aatagattga tttaaaactt c                              31

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
ttgcatgcgt aatcatggtc atagc                                     25

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
ttgaattcat gggtaataac tgatat                                    26

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
```
aaatcaatct attttcaatt caattcatca tt 32

<210> SEQ ID NO 7
<211> LENGTH: 11
<212> TYPE: DNA
<213> ORGANISM: Artificial Sequence
<220> FEATURE:
<223> OTHER INFORMATION: Primer

<400> SEQUENCE: 7
gtactaaaac c 11

<210> SEQ ID NO 8
<211> LENGTH: 11
<212> TYPE: DNA
<213> ORGANISM: Artificial Sequence
<220> FEATURE:
<223> OTHER INFORMATION: Primer

<400> SEQUENCE: 8
ccgttaaatt t 11

<210> SEQ ID NO 9
<211> LENGTH: 45
<212> TYPE: DNA
<213> ORGANISM: Artificial Sequence
<220> FEATURE:
<223> OTHER INFORMATION: Primer

<400> SEQUENCE: 9
ggatgctgtt gactccggaa atttaacggt ttggtcttgc atccc 45

<210> SEQ ID NO 10
<211> LENGTH: 14
<212> TYPE: DNA
<213> ORGANISM: Artificial Sequence
<220> FEATURE:
<223> OTHER INFORMATION: Primer

<400> SEQUENCE: 10
atgcaattta aact 14

<210> SEQ ID NO 11
<211> LENGTH: 14
<212> TYPE: DNA
<213> ORGANISM: Artificial Sequence
<220> FEATURE:
<223> OTHER INFORMATION: Primer

<400> SEQUENCE: 11
cggcaattta acgg 14

<210> SEQ ID NO 12
<211> LENGTH: 44
<212> TYPE: DNA
<213> ORGANISM: Artificial Sequence
<220> FEATURE:
<223> OTHER INFORMATION: Primer

<400> SEQUENCE: 12
ggtattgtcc tgcagacggc aatttaacgg cttctgcgaa tcgc 44

<210> SEQ ID NO 13
<211> LENGTH: 26
<212> TYPE: DNA
<213> ORGANISM: Artificial Sequence

```
<220> FEATURE:
<223> OTHER INFORMATION: Primer

<400> SEQUENCE: 13
tctgtgaggc ctatggatct cagaac                                         26

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
gatgctgcat gcacaactgc acctcag                                        27

<210> SEQ ID NO 15
<211> LENGTH: 59
<212> TYPE: DNA
<213> ORGANISM: Artificial Sequence
<220> FEATURE:
<223> OTHER INFORMATION: Primer

<400> SEQUENCE: 15
cctctagatc tcgagctcgg tcaccggtgg cctccgcggc cgctggatcc ccagttgtg     59

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
gcaagcgcgc gcaatacatg gtgttttgat cat                                 33

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
gaatgacttg gttgacgcgt caccagtcac                                     30

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
cttattagta ggttggtact tcgag                                          25

<210> SEQ ID NO 19
<211> LENGTH: 37
<212> TYPE: DNA
<213> ORGANISM: Artificial Sequence
<220> FEATURE:
<223> OTHER INFORMATION: Primer

<400> SEQUENCE: 19
gtccccagag tagtgtcact atgtcgaggc agttaag                             37
```

```
<210> SEQ ID NO 20
<211> LENGTH: 64
<212> TYPE: DNA
<213> ORGANISM: Artificial Sequence
<220> FEATURE:
<223> OTHER INFORMATION: Primer

<400> SEQUENCE: 20
gtatgtccct tgacaatgcg atgtatcaca tgatataatt actagcaagg gaagccgtgc    60
ttgg                                                                 64

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ctcccttctc tgaacaataa accc                                           24

<210> SEQ ID NO 22
<211> LENGTH: 66
<212> TYPE: DNA
<213> ORGANISM: Artificial Sequence
<220> FEATURE:
<223> OTHER INFORMATION: Primer

<400> SEQUENCE: 22
cctctagatc tcgagctcgg tcaccggtgg cctccgcggc cgctgcgcca ggtgtcagtc    60
accctc                                                               66
```

LIPOLYTIC ENZYME VARIANT

CROSS-REFERENCE TO RELATED APPLICATIONS

This application is a continuation of U.S. application Ser. No. 10/250,522 filed Jun. 30, 2003 now abandoned, which is a 35 U.S.C. 371 national application of PCT/DK02/00016, filed Jan. 10, 2002, which claims priority or the benefit under 35 U.S.C. 119 of Danish application no. PA 2001 00032 filed Jan. 10, 2001, and U.S. provisional application No. 60/262,579 filed Jan. 18, 2001, the contents of which are fully incorporated herein by reference.

FIELD OF THE INVENTION

The present invention relates to variants of fungal lipolytic enzymes, particularly variants with improved thermostability, and to methods of producing and using such variants.

BACKGROUND OF THE INVENTION

It is known to use fungal lipolytic enzymes, e.g., the lipase from *Thermomyces lanuginosus* (synonym *Humicola lanuginosa*), for various industrial purposes, e.g., to improve the efficiency of detergents and to eliminate pitch problems in pulp and paper production. In some situations, a lipolytic enzyme with improved thermostability is desirable (EP 374700, WO 92/13130).

WO 92/05249, WO 92/19726 and WO 97/07202 disclose variants of the *T. lanuginosus* (*H. lanuginosa*) lipase.

SUMMARY OF THE INVENTION

The inventors have found that the thermostability of a fungal lipolytic enzyme can be improved by certain specified substitutions in the amino acid sequence.

Accordingly, the invention provides a variant of a parent fungal lipolytic enzyme, which variant comprises substitution of one or more specified amino acid residues and is more thermostable than the parent lipolytic enzyme. The invention also provides a method of producing a lipolytic enzyme variant comprising:

a) selecting a parent fungal lipolytic enzyme, b) in the parent lipolytic enzyme substituting at least one specified amino acid residue, c) optionally, substituting one or more amino acids other than b), d) preparing the variant resulting from steps a)–c), e) testing the thermostability of the variant, f) selecting a variant having an increased thermostability, and g) producing the selected variant.

The specified amino acid residues comprise amino acid residues corresponding to any of 21, 27, 29, 32, 34–42, 51, 54, 76, 84, 90–97, 101, 105, 111, 118, 125, 131, 135, 137, 162, 187, 189, 206–212, 216, 224–234, 242–252 and 256 of SEQ ID NO: 1.

The thermostability may particularly be increased by more than 4° C. The substitutions may be with a different amino acid residue, particularly one different from Pro.

DETAILED DESCRIPTION OF THE INVENTION

Parent Lipolytic Enzyme

The lipolytic enzyme to be used in the present invention is classified in EC 3.1.1 Carboxylic Ester Hydrolases according to Enzyme Nomenclature (available at www.chem.qmw.ac.uk/iubmb/enzyme). The substrate specificity may include activities such as EC 3.1.1.3 triacylglycerol lipase, EC 3.1.1.4 phospholipase A2, EC 3.1.1.5 lysophospholipase, EC 3.1.1.26 galactolipase, EC 3.1.1.32 phospholipase A1, EC 3.1.1.73 feruloyl esterase.

The parent lipolytic enzyme is fungal and has an amino acid sequence that can be aligned with SEQ ID NO: 1 which is the amino acid sequence shown in positions 1–269 of SEQ ID NO: 2 of U.S. Pat. No. 5,869,438 for the lipase from *Thermomyces lanuginosus* (synonym *Humicola lanuginosa*), described in EP 258 068 and EP 305 216. The parent lipolytic enzyme may particularly have an amino acid sequence with at least 50% homology with SEQ ID NO: 1. In addition to the lipase from *T. lanuginosus*, other examples are a lipase from *Penicillium camembertii* (P25234), lipase/phospholipase from *Fusarium oxysporum* (EP 130064, WO 98/26057), lipase from *F. heterosporum* (R87979), lysophospholipase from *Aspergillus foetidus* (W33009), phospholipase A1 from *A. oryzae* (JP-A 10-155493), lipase from *A. oryzae* (D85895), lipase/ferulic acid esterase from *A. niger* (Y09330), lipase/ferulic acid esterase from *A. tubingensis* (Y09331), lipase from *A. tubingensis* (WO 98/45453), lysophospholipase from *A. niger* (WO 98/31790), lipase from *F. solanii* having an isoelectric point of 6.9 and an apparent molecular weight of 30 kDa (WO 96/18729).

Other examples are the Zygomycetes family of lipases comprising lipases having at least 50% homology with the lipase of *Rhizomucor miehei* (P19515) having the sequence shown in SEQ ID NO: 2. This family also includes the lipases from *Absidia reflexa, A. sporophora, A. corymbifera, A. blakesleeana, A. griseola* (all described in WO 96/13578 and WO 97/27276) and *Rhizopus* oryzae (P21811). Numbers in parentheses indicate publication or accession to the EMBL, GenBank, GeneSeqp or Swiss-Prot databases.

Amino Acid Substitutions

The lipolytic enzyme variant of the invention comprises one or more substitutions of an amino acid residue in any of the regions described above. The substitution may, e.g., be made in any of the regions corresponding to 206–208, 224–228, 227–228, 227–231, 242–243 and 245–252 of SEQ ID NO: 1. The amino acid residue to be substituted may correspond to residue Y21, D27, P29, T32, A40, F51, S54, I76, R84, I90, G91, N94, N101, S105, D111, R118, R125, A131, H135, D137, N162, V187, T189, E210, G212, S216, G225, L227, I238 or P256 of SEQ ID NO: 1. Some particular substitutions of interest are those corresponding to D27N/R/S, P29S, T32S, F51I/L, I76V, R84C, I90L/V, G91A/N/S/T/W, L93F, N94K/R/S, F95I, D96G/N, N101D, D111A/G, R118M, A131V, H135Y, D137N, N162R, V187I, F211Y, S216P, S224I/Y, G225P, T226N, L227F/P/G/V, L227X, V228C/I, 238V and P256T of SEQ ID NO: 1.

The total number of substitutions in the above regions is typically not more than 10, e.g., one, two, three, four, five, six, seven or eight of said substitutions. In addition, the lipolytic enzyme variant of the invention may optionally include other modifications of the parent enzyme, typically not more than 10, e.g., not more than 5 such modifications.

The variant may particularly have a total of not more than 10 amino acid modifications (particularly substitutions) compared to the parent lipolytic enzyme. The variant generally has a homology with the parent lipolytic enzyme of at least 80%, e.g., at least 85%, typically at least 90% or at least 95%.

Lipolytic Enzyme Variant

The variant has lipolytic enzyme activity, i.e., it is capable of hydrolyzing carboxylic ester bonds to release carboxylate (EC 3.1.1). It may particularly have lipase activity (triacylglycerol lipase activity, EC 3.1.1.3), i.e., hydrolytic activity for carboxylic ester bonds in triglycerides, e.g., 1,3-specific activity.

Specific Variants

The following are some examples of variants of the *T. lanuginosus* lipase. Corresponding substitutions may be made by making corresponding amino acid substitutions in other fungal lipolytic enzymes:

D27N
D111G + S216P
L227F
L227F + V228I
G225P
S224I + G225W + T226N + L227P + V228C
S224Y + G225W + T226N + L227P + V228C
D27R + D111G + S216P
D27S + D111G + S216P
D27N + D111A
D27R + D111G + S216P + L227P + P256T
D27R + D111G + S216P + L227G + P256T
D27R + D111G + S216P + L227F + P256T
D27R + D111G + S216P + L227V + P256T
D27R + D111G + S216P + L227G
D27R + D111G + S216P + L227X
D27P + D111G + S216P + L227X

Thermostability

The thermostability can be measured at a relevant pH for the intended application using a suitable buffer. Examples of buffers and pH are: pH 10.0 (50 mM glycine buffer), pH 7.0 (50 mM HEPES Buffer) or pH 5.0 (50 mM sodium acetate as buffer).

For comparison, measurements should be made in the same buffer, at the same conditions and at the same protein concentration. Various methods can be used for measuring the thermostability:

Differential Scanning Calorimetry (DSC)

In DSC, the heating rate may be 90 degrees per hour. The sample may be purified to homogeneity, and the melting temperature ($T_M$) may be taken as an expression of the thermostability.

Residual Enzyme Activity

Alternatively, the thermostability can be determined by measuring residual lipolytic enzyme activity after incubation at selected temperatures. p-nitrophenyl ester in 10 mM Tris-HCl, pH 7.5 may be used as the substrate, as described in Giver et al., *Proc. Natl. Acad. Sci. USA,* 95: 12809–12813 (1998) and Moore et al., *Nat. Biotech.,* 14: 458–467 (1996). Samples may be added periodically, or only one sample may be used with or without different additives to prevent or enhance denaturing, e.g., in a 96 well format.

CD Spectroscopy

CD spectroscopy as described, e.g., in Yamaguchi et al., *Protein Engineering,* 9: 789–795 (1996). Typical enzyme concentration is around 1 mg/ml and temperature is between 5–80 degrees.

Use of Variant

The lipolytic enzyme variants may be used in various processes, and some particular uses are described below. The variant is typically used at 60–95° C. (particularly 75–90° C., 70–90° C. or 70–85° C.) and pH 4.5–11 (particularly 4.5–8 or 5–6.5).

Use in the Paper and Pulp Industry

The lipase may be used in a process for avoiding pitch troubles in a process for the production of mechanical pulp or a paper-making process using mechanical pulp, which comprises adding the lipase to the pulp and incubating. The lipase addition may take place in the so-called white water (recycled process water). It may also be used to remove ink from used paper. The improved thermostability allows the variant to be used at a higher temperature, generally preferred in the industry. This may be done in analogy with WO 92/13130, WO 92/07138, JP 2160984 A, or EP 374700.

Use in Cereal-Based Food Products

The lipolytic enzyme variant may be added to a dough, and the dough may be used to prepare a baked product (particularly bread), pasta or noodles. The improved thermostability of the variant allows it to remain active for a longer time during the heating step (baking, boiling or frying). This may be done in analogy with WO 94/04035, WO 00/32758, PCT/DK01/00472, or EP 1057415.

The addition of the variant may lead to improved dough stabilization, i.e., a larger loaf volume of the baked product and/or a better shape retention during baking, particularly in a stressed system, e.g., in the case of over-proofing or over-mixing. It may also lead to a lower initial firmness and/or a more uniform and fine crumb, improved crumb structure (finer crumb, thinner cell walls, more rounded cells), of the baked product, and it may further improve dough properties, e.g., a less soft dough, higher elasticity, lower extensibility.

Use in the Fat and Oil Industry

The lipolytic enzyme variant may be used as a catalyst in organic synthesis, e.g., in a process for hydrolyzing, synthesizing or interesterifying an ester, comprising reacting the ester with water, reacting an acid with an alcohol or interesterifying the ester with an acid, an alcohol or a second ester in the presence of the lipolytic enzyme variant. Favorably, the improved thermostability allows the process to be conducted at a relatively high temperature which may be favorable to increase the rate of reaction and to process high-melting substrates.

The ester may be a carboxylic acid ester, e.g., a triglyceride. The interesterification may be done in the presence or absence of a solvent. The enzyme may be used in immobilized form. The process may be conducted in analogy with WO 88/02775, U.S. Pat. No. 6,156,548, U.S. Pat. No. 5,776,741, EP 792106, EP 93602, or EP 307154.

Use in Textile Industry

The variant may be used in a process for enzymatic removal of hydrophobic esters from fabrics, which process comprises treating the fabric with an amount of the lipolytic enzyme effective to achieve removal of hydrophobic esters from fabric. The treatment may be done at a temperature of 75° C. or above, e.g., for a period of 1–24 hours. The treatment may be preceded by impregnating the fabric with an aqueous solution of the lipase variant to a liquor pick-up ratio of 50–200%, and may be followed by washing and rinsing to remove the fatty acids.

The process may be conducted in analogy with U.S. Pat. No. 5,578,489 or U.S. Pat. No. 6,077,316.

Use in Detergents

The variant may be used as a detergent additive, e.g., at a concentration (expressed as pure enzyme protein) of 0.001–10 (e.g., 0.01–1) mg per gram of detergent or 0.001–100 (e.g., 0.01–10) mg per liter of wash liquor. This may be done in analogy with WO 97/04079, WO 97/07202, WO 97/41212, WO 98/08939 and WO 97/43375.

Use for Leather

The variants of the invention can also be used in the leather industry in analogy with GB 2233665 or EP 505920.

Nomenclature for Amino Acid Substitutions

The nomenclature used herein for defining amino acid substitutions uses the single-letter code, as described in WO 92/05249.

Thus, D27N indicates substitution of D in position 27 with N. D27N/R indicates a substitution of D27 with N or R. L227X indicates a substitution of L227 with any other amino acid. D27N+D111A indicates a combination of the two substitutions.

Homology and Alignment

For purposes of the present invention, the degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis. 53711) (Needleman, and Wunsch, *Journal of Molecular Biology*, 48: 443–45 (1970)), using GAP with the following settings for polypeptide sequence comparison: GAP creation penalty of 3.0 and GAP extension penalty of 0.1.

In the present invention, corresponding (or homologous) positions in the lipase sequences of *Rhizomucor miehei* (rhimi), *Rhizopus delemar* (rhidl), *Thermomyces lanuginosa* (former; *Humicola lanuginosa*) (SP400), *Penicillium camembertii* (Pcl) and *Fusarium oxysporum* (FoLnp11), are defined by the alignment shown in FIG. 1 of WO 00/32758.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis. 53711) (Needleman and Wunsch, *Journal of Molecular Biology*, 48: 443–45 (1970)). The following settings are used for polypeptide sequence comparison: GAP creation penalty of 3.0 and GAP extension penalty of 0.1.

Procedure for Obtaining Thermostable Variants

Variants of a lipolytic enzyme can be obtained by methods known in the art, such as site-directed mutagenesis, random mutagenesis or localized mutagenesis, e.g., as described in WO 95/22615 or WO 00/32758.

Thermostable variants of a given parent lipolytic enzyme can be obtained by the following standard procedure:
  Mutagenesis (error-prone, doped oligo, spiked oligo)
  Primary Screening
  Identification of more temperature stable mutants
  Maintenance (glycerol culture, LB-Amp plates, Mini-Prep)
  Streaking out on another assay plate—secondary screening (1 degree higher then primary screening)
  DNA Sequencing
  Transformation in *Aspergillus*
  Cultivation in 100 ml scale, purification, DSC Primary Screening Assay The following assay method is used to screen lipolytic enzyme variants and identify variants with improved thermostability.

*E. coli* cells harboring variants of a lipolytic enzyme gene are prepared, e.g., by error-prone PCR, random mutagenesis or localized random mutagenesis or by a combination of beneficial mutants and saturation mutagenesis.

The assay is performed with filters on top of a LB agar plate. *E. coli* cells are grown on cellulose acetate filters supplied with nutrients from the LB agar plate and under the selection pressure of ampicillin supplied with the LB agar. Proteins including the desired enzyme are collected on a nitrocellulose filter between LB agar and cellulose acetate filter. This nitrocellulose filter is incubated in a buffer of desired pH (generally 6.0) and at the desired temperature for 15 minutes (e.g., 78 degrees for the *T. lanuginosus* lipase). After quenching the filters in ice-water, the residual lipase activity is determined through the cleavage of indole acetate and the subsequent coloration of the reaction product with nitro-blue tetrazolium chloride as described by Kynclova et al. (*Journal of Molecular Recognition*, 8: 139–145 (1995)).

The heat treatment applied is adjusted so that the parent generation is slightly active, approximately 5–10% compared to samples incubated at room temperature. This facilitates the identification of beneficial mutants.

EXAMPLES

Example 1

Expression of Lipase

Plasmid pMT2188

The *Aspergillus oryzae* expression plasmid pCaHj483 (WO 98/00529) consists of an expression cassette based on the *Aspergillus niger* neutral amylase II promoter fused to the *Aspergillus nidulans* triose phosphate isomerase non translated leader sequence (Pna2/tpi) and the *A. niger* amyloglycosidase terminater (Tamg). Also present on the plasmid is the *Aspergillus* selective marker amdS from *A. nidulans* enabling growth on acetamide as sole nitrogen source. These elements are cloned into the *E. coli* vector pUC19 (New England Biolabs). The ampicillin resistance marker enabling selection in *E. coli* of this plasmid was replaced with the URA3 marker of *Saccharomyces cerevisiae* that can complement a pyrF mutation in *E. coli*, the replacement was done in the following way:

The pUC19 origin of replication was PCR amplified from pCaHj483 with the primers 142779 (SEQ ID NO: 3) and 142780 (SEQ ID NO: 4).

Primer 142780 introduces a BbuI site in the PCR fragment. The Expand PCR system (Roche Molecular Biochemicals, Basel, Switserland) was used for the amplification following the manufacturers instructions for this and the subsequent PCR amplifications.

The URA3 gene was amplified from the general *S. cerevisiae* cloning vector pYES2 (Invitrogen corporation, Carlsbad, Calif., USA) using the primers 140288 (SEQ ID NO: 5) and 142778 (SEQ ID NO: 6).

Primer 140288 introduces an EcoRI site in the PCR fragment. The two PCR fragments were fused by mixing them and amplifying using the primers 142780 and 140288 in the splicing by overlap method (Horton et al., *Gene*, 77: 61–68 (1989)).

The resulting fragment was digested with EcoRI and BbuI and ligated to the largest fragment of pCaHj483 digested with the same enzymes. The ligation mixture was used to transform the pyrF *E. coli* strain DB6507 (ATCC 35673) made competent by the method of Mandel and Higa (Mandel and Higa, *J. Mol. Biol.*, 45: 154 (1970)). Transformants were selected on solid M9 medium (Sambrook et al., Molecular Cloning, A Laboratory Manual, 2nd edition, Cold Spring Harbor Laboratory Press (1970)) supplemented with 1 g/l casaminoacids, 500 micrograms/l thiamine and 10 mg/l kanamycin.

A plasmid from a selected transformant was termed pCaHj527. The Pna2/tpi promoter present on pCaHj527 was subjected to site directed mutagenesis by a simple PCR approach.

Nucleotides 134–144 were altered from SEQ ID NO: 7 to SEQ ID NO: 8 using the mutagenic primer 141223 (SEQ ID NO: 9).

Nucleotides 423–436 were altered from SEQ ID NO: 10 to SEQ ID NO: 11 using the mutagenic primer 141222 (SEQ ID NO: 12).

The resulting plasmid was termed pMT2188.

Plasmid pENI1849

Plasmid pENI1849 was made in order to truncate the pyrG gene to the essential sequences for pyrG expression, in order to decrease the size of the plasmid, thus improving transformation frequency. A PCR fragment (approximately 1800 bp) was made using pENI1299 (described in WO 00/24883) as template and the primers 270999J8 (SEQ ID NO: 13) and 270999J9 (SEQ ID NO: 14).

The PCR-fragment was cut with the restriction enzymes StuI and SphI, and cloned into pENI1298 (described in WO 00/24883), also cut with StuI and SphI; the cloning was verified by sequencing.

Plasmid pENI1861

Plasmid pENI1861 was made in order to have the state of the art *Aspergillus* promoter in the expression plasmid, as well as a number of unique restriction sites for cloning.

A PCR fragment (approximately 620 bp) was made using pMT2188 (see above) as template and the primers 051199J1 (SEQ ID NO: 15) and 1298TAKA (SEQ ID NO: 16).

The fragment was digested with Bss HII and Bgl II, and cloned into pENI1849 which was also digested with Bss HII and Bgl II. The cloning was verified by sequencing.

Plasmid pENI1902

Plasmid pENI1902 was made in order to have a promoter that works in both *E. coli* and *Aspergillus*. This was done by unique site elimination using the "Chameleon double stranded site-directed mutagenesis kit" as recommended by Stratagene®.

Plasmid pENI1861 was used as the template and the following primers with 5' phosphorylation were used as selection primers: 177996 (SEQ ID NO: 17), 135640 (SEQ ID NO: 18) and 135638 (SEQ ID NO: 19).

The 080399J19 primer (SEQ ID NO: 20) with 5' phosphorylation was used as mutagenic primer to introduce a −35 and −10 promoter consensus sequence (from *E. coli*) in the *Aspergillus* expression promoter. Introduction of the mutations was verified by sequencing.

Plasmid psMin001

Plasmid psMin001 was made in order to permit the expression of the *T. lanuginosus* lipase in *E. coli* and *Aspergillus*.

Plasmid pAHL (described in WO 92/05249) was used as template for PCR to amplify the *T. lanuginosus* lipase gene with the following Primers: 19671 (SEQ ID NO: 21) and 991213J5 (SEQ ID NO: 22). Primer 991213J5 introduced a SacII site into the PCR fragment. The PCR fragment (approximately 1100 bp) was cut with BamHI and SacII and cloned into pEni1902 digested with the same enzymes. The cloning was verified by DNA sequencing. The plasmid was transformed in *E. coli* DH5α, and lipase expression was detected by using the described filter assay.

Using this newly developed plasmid it was possible to express the desired enzyme in *Aspergillus* without any modification. The achieved expression rates in *E. coli* were quite low, but sufficient for the screening assay.

Example 2

Production of Thermostable Lipase Variants

Several techniques were used to create diversity in the *T. lanuginosus* lipase gene: error-prone PCR, localized random mutagenesis with the aid of doped oligonucleotides, and site-directed mutagenesis.

Variants exhibiting higher temperature stability were selected by the primary assay described above, and were cultivated in LB media and streaked out again on assay plates as described above for a secondary screening. The assay in the secondary screening was performed with a 1–1.5 degrees higher temperature. The DNA of mutants still active under these conditions were sequenced and transformed into *Aspergillus* to obtain a higher amount of protein, followed by a chromatographic purification. The purified enzyme was used for DSC analysis to prove the enhancement of the stability.

Next, amino acid substitutions found in the beneficial variants were combined, and saturation mutagenesis was used to ensure that all 20 amino acids were introduced in the desired positions.

Example 3

Thermostability of Lipase Variants

All samples identified as more thermostable in the primary and secondary screening in Example 2 were purified to homogeneity, and their stability was checked by differential scanning calorimetry (DSC) at pH 5.0 and/or 7.0 to determine the stability of the protein, given by its melting temperature ($T_M$). The parent lipase from *T. lanuginosus* was included for comparison.

Eight variants were found to have increased thermostability at pH 5.0, four variants showing an increase of more than 4° C. Two variants were tested at pH 7.0 and found to have improved thermostability.

Example 4

Thermostability of Lipase Variants by DSC

A number of variants of the *T. lanuginosus* lipase were prepared and purified, and the thermostability was checked by differential scanning calorimetry (DSC) at pH 5.0 to determine the stability of the protein, given by its melting temperature ($T_M$). The parent lipase from *T. lanuginosus* was included for comparison.

The following variants were found to be more thermostable than the parent lipase:

D111G+S216P
D27N
L227F
S224I+G225W+T226N+L227P+V228C
L227F+V228I
G225P
W221C+G246C

The following variants were found to be more thermostable than the parent lipase with at least 4° C. increase of the melting temperature.

D27R + D111G + S216P
D27N + D111A
D27R + D111G + S216P + L227G + P256T
D27R + D111G + S216P + L227F + P256T
D27R + D111G + S216P + L227G
D27S + D111G + S216P
D27R + D111A + S216P + L227G + P256T
D27R + D111G + S216P + G225P + L227G + P256T
D27R + T37S + D111G + S216P + L227G + P256T
D27R + N39F + D111G + S216P + L227G + P256T
D27R + G38C + D111G + S216P + L227G + P256T
D27R + D111G + S216P + L227G + T244I + P256T
D27R + G91A + D111G + S216P + L227G + P256T
N25I + D27R + D111A + S216P + L227G + P256T
N25L + D27R + D111A + S216P + L227G + P256T
N26D + D27R + D111A + S216P + L227G + P256T
D27R + K46R + D111A + S216P + L227G + P256T
D27R + V60N + D111A + S216P + L227G + P256T
D27R + D111A + P136A + S216P + L227G + P256T
D27R + D111A + S216P + L227G + P256T + I265F
D27R + S58Y + D111A + S216P + L227G + P256T
N26D + D27R + E56Q + D111A + S216P + L227G + P256T
D27R + G91A + D96E + L97Q + D111A + S216P + L227G + P256T
D27R + G91A + D111A + S216P + L227G + P256T
D27R + G91T + N94S + D111A + S216P + L227G + P256T
D27R + G91S + D111A + S216P + L227G + P256T
D27R + G91N + D111A + S216P + L227G + P256T
D27R + D96E + D111A + S216P + L227G + P256T
D27R + I90L + G91A + N94K + D111A + S216P + L227G + P256T
D27R + G91S + F95V + D111A + S216P + L227G + P256T

Example 5

Thermostability by Plate Assay

A number of variants of the *T. lanuginosus* lipase were prepared and tested for thermostability as described above under "primary screening assay". The parent lipase from *T. lanuginosus* was included for comparison.

The following variants were found to be more thermostable than the parent lipase:

D27R + I90V + G91S + D111A + S216P + L227G + P256T
D27R + G91N + N94R + D111A + S216P + L227G + P256T
D27R + I90L + L93F + D96N + D111A + S216P + L227G + P256T
D27R + I90L + G91A + D96E + D111A + S216P + L227G + P256T
D27R + G91S + L93F + D111A + S216P + L227G + P256T
D27R + G91T + N94K + D111A + S216P + L227G + P256T
D27R + G91T + D111A + S216P + L227G + P256T
D27R + L93F + D111A + D137N + S216P + L227G + P256T
D27R + G91S + D96N + D111A + S216P + L227G + P256T
D27R + G91W + D111A + S216P + L227G + P256T
D27R + I90L + G91T + D111A + S216P + L227G + P256T
D27R + G91S + L93F + N94R + D96G + D111A + S216P + L227G + P256T
D27R + G91T + D96N + D111A + S216P + L227G + P256T
D27R + I90V + G91T + L93F + N94K + D111A + S216P + L227G + P256T
D27R + L93V + D111A + S216P + L227G + P256T
D27R + G91S + N94K + D111A + S216P + L227G + P256T
D27R + I90L + G91T + D111A + S216P + L227G + P256T
D27R + G91S + L93F + F95I + D96N + D111A + S216P + L227G + P256T
D27R + D111A + V187I + S216P + L227G + P256T
D27R + D111A + F211Y + S216P + L227G + P256T
D27R + R118M + D111A + A131V + S216P + L227G + P256T
D27R + P29S + R84C + D111A + H135Y + S216P + L227G + P256T
D27R + T32S + D111A + H135Y + S216P + L227G + P256T
D27R + G91R + D111A + I238V + S216P + L227G + P256T
D27R + F51I + I76V + N101D + D111A + N162R + S216P + L227G + P256T
D27R + F51L + D111A + S216P + L227G + P256T

---

The invention claimed is:

1. A variant of the parent fungal lipolytic enzyme having the amino acid sequence of SEQ ID NO: 1, wherein the variant has an amino acid sequence having at least 90% homology with SEQ ID NO: 1 and comprises one or more of the following substitutions: P29S, T32S, F51I/L, R84C, I90L, G91N/S/W, L93F, F95I, N101D, R118M, H135Y, N162R, V187I, T226N, L227F/P/G/V, or V228C.

2. The variant of claim 1, which has at least 95% homology with SEQ ID NO: 1.

3. The variant of claim 1, which comprises one, two, three, four, five, six, seven or eight of said substitutions.

4. The variant of claim 1, which has 10 or less amino acid substitutions compared to SEQ ID NO: 1.

5. The variant of claim 1, wherein the variant further comprises one or more of the following substitutions: D27N/R/S, I76V, I90V, G91A/T, N94K/R/S, D96G/N, D111A/G, A131V, D137N, F211Y, S216P, S224I/Y, G225P, V228I, I238V, or P256T.

6. The variant of claim 1, wherein the variant comprises one of the following sets of mutations:
N25I+D27R+D111A+S216P+L227G+P256T;
N25L+D27R+D111A+S216P+L227G+P256T;
N26D+D27R+E56Q+D111A+S216P+L227G+P256T;
N26D+D27R+D111A+S216P+L227G+P256T;
D27R+T37S+D111G+S216P+L227G+P256T;
D27R+G38C+D111G+S216P+L227G+P256T;
D27R+N39F+D111G+S216P+L227G+P256T;
D27R+K46R+D111A+S216P+L227G+P256T;
D27R+S58Y+D111A+S216P+L227G+P256T;
D27R+V60N+D111A+S216P+L227G+P256T;
D27R+I90L+G91A+N94K+D111A+S216P+L227G+P256T;
D27R+G91A+D96E+L97Q+D111A+S216P+L227G+P256T;
D27R+G91A+D111A+S216P+L227G+P256T;
D27R+G91A+D111G+S216P+L227G+P256T;
D27R+G91N+N94R+D111A+S216P+L227G+P256T;
D27R+G91N+D111A+S216P+L227G+P256T;
D27R+G91S+F95V+D111A+S216P+L227G+P256T;
D27R+G91S+D111A+S216P+L227G+P256T;
D27R+G91T+N94S+D111A+S216P+L227G+P256T;
D27R+D96E+D111A+S216P+L227G+P256T;
D27R+D111A+P136A+S216P+L227G+P256T;
D27R+D111A+S216P+L227G+P256T;
D27R+D111A+S216P+L227G+P256T+I265F;
D27R+D111G+S216P+G225P+L227G+P256T;
D27R+D111G+S216P+L227F+P256T;
D27R+D111G+S216P+L227G;
D27R+D111G+S216P+L227G+T244I+P256T;
D27R+D111G+S216P+L227G+P256T;
D27R+D111G+S216P+L227P+P256T;
D27R+D111G+S216P+L227V+P256T;
S224I+G225W+T226N+L227P+V228C;
S224Y+G225W+T226N+L227P+V228C;
L227F; and
L227F+V228I.

7. The variant of claim 1, wherein the variant comprises the following substitutions: D27R+G91N+N94R+D111A+S216P+L227G+P256T.

8. The variant of claim 1, wherein the variant is more thermostable than the parent lipolytic enzyme.

9. The variant of claim 1, wherein the variant is at least 4° C. more thermostable than the parent lipolytic enzyme.

10. The variant of claim 1, wherein the variant has a denaturation temperature which is at least 5° C. higher than the parent lipolytic enzyme.

11. A detergent composition comprising a variant of claim 1 and a surfactant.

12. A process for controlling pitch troubles in a process for the production of mechanical pulp or a paper-making process using mechanical pulp, which comprises adding a variant of claim 1 to the pulp and incubating.

13. A process for removing a hydrophobic ester from a fabric, comprising treating the fabric with an amount of a variant of claim 1 effective for removing the hydrophobic ester.

14. A process for preparing a baked product, comprising
a) treating the dough with a variant of claim 1; and
b) baking the dough.

15. A process for hydrolyzing or synthesizing an ester, comprising reacting the ester with water, or reacting an acid with an alcohol, or reacting the ester with an acid, an alcohol or a second ester in the presence of a variant of claim 1.

16. A DNA sequence encoding the variant of claim 1.

17. A vector comprising the DNA sequence of claim 16.

18. A transformed host cell harboring the DNA sequence of claim 16.

19. A method of producing a lipase variant, comprising
a) cultivating the cell of claim 18 so as to express the variant, and
b) recovering the variant.

* * * * *